(12) United States Patent
Lane et al.

(10) Patent No.: US 6,213,984 B1
(45) Date of Patent: Apr. 10, 2001

(54) SELF-METERING CARTRIDGE

(76) Inventors: Donovan R. Lane, P. O. Box 544, Paso Robles, CA (US) 93447; John Main, Private Bag 3126, Hamilton (NZ); Peter Murphy, 93 Dominion Road Mt. Eden, Auckland (NZ)

( * ) Notice: Subject to any disclaimer, the term of this patent is extended or adjusted under 35 U.S.C. 154(b) by 0 days.

(21) Appl. No.: 09/351,558

(22) Filed: Jul. 12, 1999

Related U.S. Application Data
(60) Provisional application No. 60/093,166, filed on Jul. 17, 1998.

(51) Int. Cl.[7] ............................................. A61M 5/00
(52) U.S. Cl. ................................................. 604/207
(58) Field of Search ............................ 604/207–210, 604/218, 223, 224, 228, 232–235, 246, 187

(56) References Cited

U.S. PATENT DOCUMENTS

| | | | |
|---|---|---|---|
| 5,190,191 | * 3/1993 | Reyman | 222/256 |
| 5,733,258 | * 3/1998 | Lane | 604/51 |
| 5,759,171 | * 6/1998 | Coelho et al. | 604/82 |
| 5,964,736 | * 10/1999 | Lane | 604/220 |

* cited by examiner

*Primary Examiner*—Sharon Kennedy
*Assistant Examiner*—Ann Y. Lam
(74) *Attorney, Agent, or Firm*—Dean P. Edmundson

(57) ABSTRACT

A cartridge and system are described for automatically metering a predetemined dosage of a medicament. The cartridge includes a tab on its exterior, and a dispensing gun which receives the cartridge has a detent for stopping forward movement of the upper end of a trigger when the detent contacts the tab on the cartridge. When the detent contacts the tab on the cartridge, no further medicament can be dispensed on that stroke of the trigger.

5 Claims, 4 Drawing Sheets

SELF-METERING CARTRIDGE

CROSS-REFERENCE TO RELATED APPLICATION

This application is based upon, and claims the benefit of, our U.S. Provisional Application Ser. No. 60/093,166, filed Jul. 17, 1998.

BACKGROUND

1. Field of Invention

This invention relates to multidose, medical injection syringes used for the vaccination and treatment of livestock diseases. More specifically, it relates to a process and a closed handling and delivery system for those injectable animal health products used in syringes and how the dosage level administered to the patient is controlled or metered.

2. Description of Prior Art

Generally speaking, in multidose, pistol grip livestock syringes, the precise metering of the dosage dispensed is accomplished by restricting the stroke of the plunger rod. Heretofore, the stroke of the plunger rod has been controlled by mechanical systems incorporated into the syringe body and trigger mechanisms. Original designs of pistol grip syringes commonly include ratchet and pawl mechanisms, wherein the trigger is squeezed and a pawl attached to the trigger engages a ratchet, formed on the plunger rod. The plunger rod is then advanced forward to dispense the medicament from the barrel of the syringe.

Metering is accomplished by an adjustable stop attached to either the trigger, as is demonstrated in U.S. Pat. No. 3,110,310 to Cislak (1963), or to the syringe body as is shown in U.S. Pat. 4,014,331 to Head (1977). The adjustable stop restricts the forward movement or stroke of the plunger rod, therefore metering the amount of medicament dispensed. Similar mechanisms for dosage metering are employed when pre-filled cartridges are used with pistol grip syringe bodies as is shown in U.S. Pat. No. 4,738,664 to Prindle (1988) and U.S. Pat. No. 3,517,668 to Brickson (1967).

Phillips et al. (1988), in U.S. controlled by a threaded adjustment on the anterior end of the syringe body. Other known cartridge type systems generally utilize a single dose system wherein one full squeeze of the trigger dispenses the entire contents of the cartridge as is shown in U.S. Pat. No. 4,576,591 to Kaye et al. (1986) and U.S. Pat. No. 4,968,303 to Clarke et al. (1990).

With those methods of dosage metering, the amount of medicament dispensed from a multi-dose cartridge is determined by a setting or an adjustment made to the syringe or applicator by the technician. Mechanical dosage settings are often bumped or may slip to the next setting so that many animals may be injected with the improper dosage before the mistake has been detected and the correction is made. It is also not uncommon for the technician to accidentally set the dosage adjustment to an improper setting. Most medicaments have a prescribed dosage level, which technically could eliminate the need for dosage adjustment by the technician.

There has not heretofore been provided a self-metering cartridge system or a system for automatically metering a predetermined dosage of a medicament from a cartridge.

SUMMARY OF THE PRESENT INVENTION

Dosage levels for most medicaments, particularly vaccines, are constant and prescribed by the manufacturer of the vaccine. As an example, a vaccine for the prevention of X disease may require a 5 milliliter dose while a different vaccine for Y disease may prescribe a 2 milliliter dose. In our self-metering cartridge system, all syringe bodies are capable of dispensing any dosage level up to the largest dosage that may be prescribed. The self-metering cartridge will dictate the length of the stroke of the plunger rod therefore dictating the dosage level of the medicament dispensed with each squeeze of the trigger.

In practice, a 2-milliliter dose product will be packaged in a self-metering cartridge that will restrict the forward movement of the plunger rod and allow precisely 2 milliliters of medicament to be dispensed from the cartridge. Similarly a 5-milliliter dose self-metered cartridge will stop the forward movement of the plunger rod when 5 milliliters of medicament have been dispensed from the cartridge. If the loaded cartridge in the chamber is not equipped with the self-metering aspect, a full squeeze of the trigger will allow the plunger rod to advance as far forward as is mechanically possible. That full squeeze will dictate the largest dosage that the syringe is capable of administering. As an example, an unrestricted full squeeze may dispense 10 milliliters of medicament.

The advantage to the self-metering cartridge is that no human error or mechanical malfunction of an adjustable metering mechanism can cause the syringe to give an improper dosage. Even if the wrong medicament has been accidentally loaded into the syringe, the proper dosage for that particular medicament will be given. In addition, the stop mechanism for metering the dosage level has bene simplified to no adjustable or moving parts. When a cartridge is loaded into the barrel of a syringe body, the metering is automatic and specific to the product contained in the cartridge.

Other features and advantages of the present invention will be apparent from the following detailed description and the accompanying drawings.

BRIEF DESCRIPTION OF THE DRAWINGS

FIG. 1A is an enlargement of a portion of FIG. 1;

FIG. 2A is an enlargement of a portion of FIG. 2;

Figure 1:
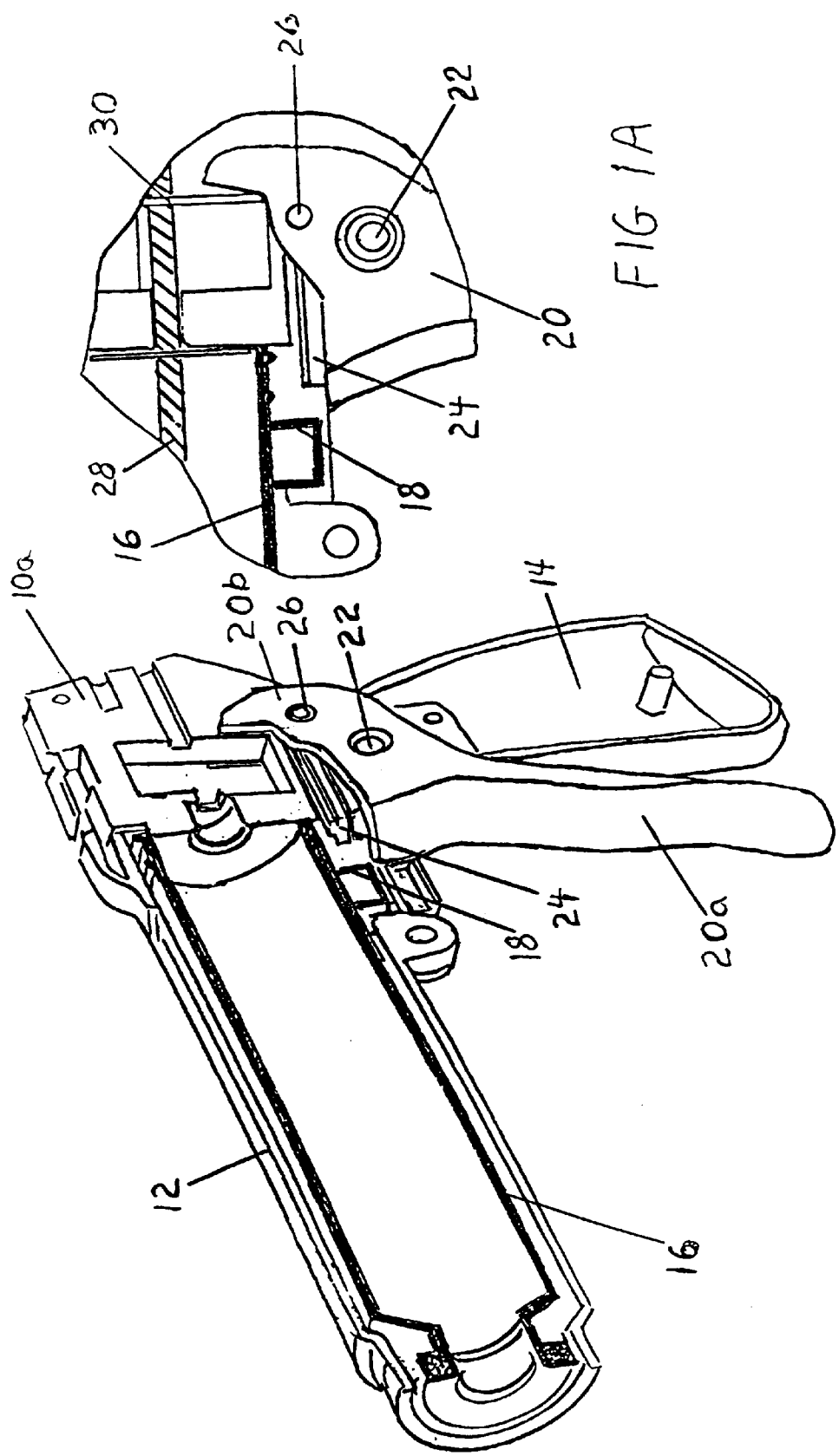
FIG. 1 shows a pistol grip syringe body with the trigger in the resting position.

REFERENCE NUMERALS IN DRAWINGS 10a syringe body frame, right half
10b syringe body frame, left half
12 syringe body barrel
14 syringe body handle
16 self-metering cartridge
18 cartridge metering tab
20 trigger
20a lower trigger
20b upper trigger
22 trigger pivot
24 moveable metering rod
26 metering rod hinge point
28 plunger rod 30 drag link
32 plunger
34 tear away foil seal
36 standard rubber stopper
38 standard aluminum stopper seal

DETAILED DESCRIPTION OF THE
INVENTION

The essence of this invention combines the mechanical aspects of the items shown in FIGS. 1 through 4 to complement the systems described in U.S. Pat. No. 5,733,258 and application Ser. No. 08/532,055, incorporated herein by reference. The goals of this self-metering cartridge are as follows:
  (a) simplify the mechanism to automatically meter the dosage given by this syringe and cartridge system.
  (b) eliminate the need to preset or adjust the syringe to meter the dosage to be given.
  (c) eliminate the chance of human or mechanical error often associated with mechanical hand adjustments of the syringe to meter the dosage levels.
  (d) transfer the responsibility of dosage metering from the syringe body to the cartridge. Therefore, a medicament will be packaged into a self-metering cartridge, pre-set to the dosage level prescribed by the manufacturer of the medicament. No adjustments need to be or can be made by the technician administering the medicament to the livestock; therefore, the proper dosage level is always given.
  (e) reduce the cost to manufacture the metering devise in the syringe.

Figure 2:
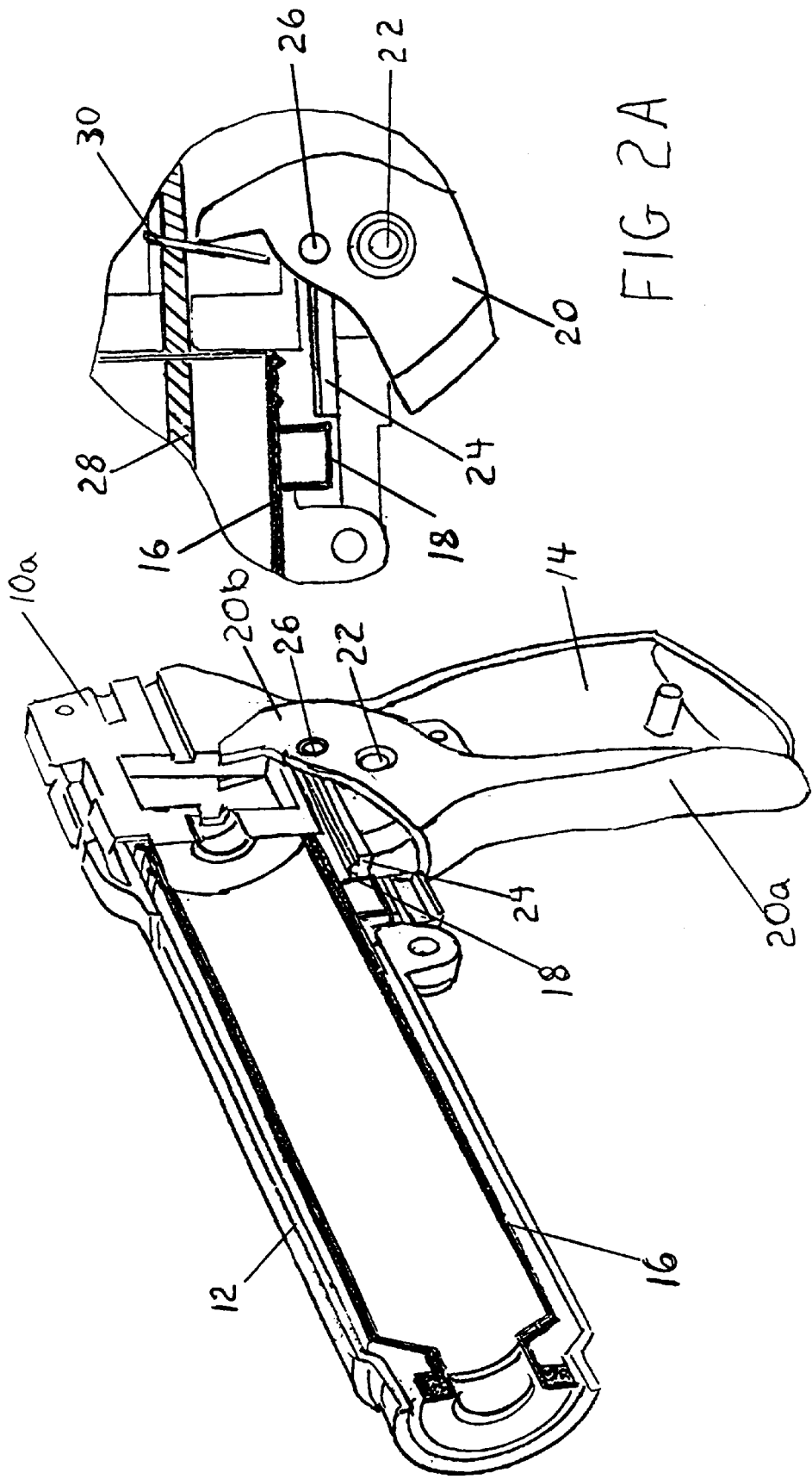
FIG. 2 shows the syringe body of FIG. 1 with the trigger in the squeezed position.
Figure 3:
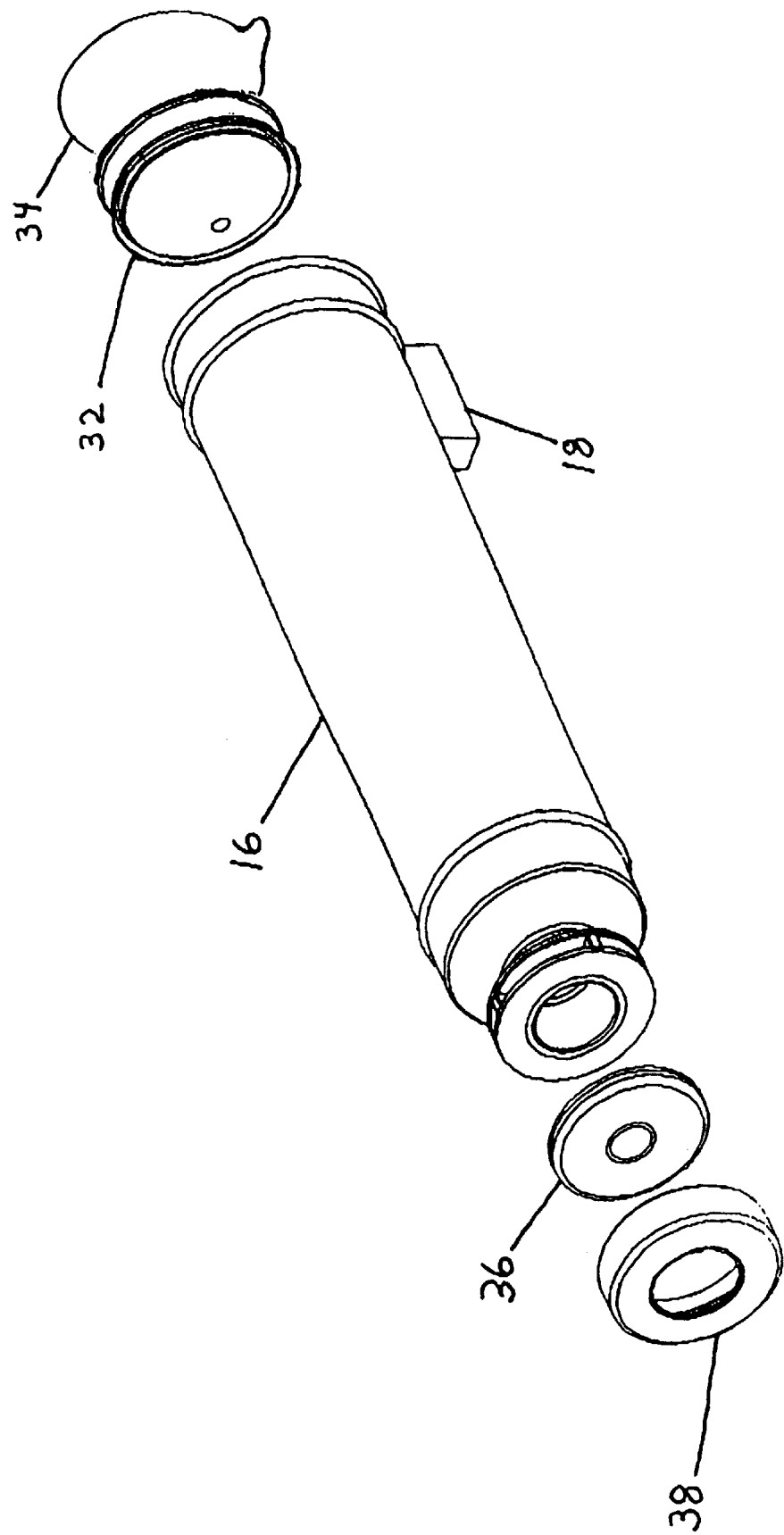
FIG. 3 is the cartridge with the metering tab.

A preferred embodiment of the self-metering cartridge is illustrated in FIG. 1 through 4. The disposable, self-metering cartridge 16, as shown in FIG. 3, is a cylindrical hollow tube made of a durable or unbreakable, plastic-like substance. The anterior end is necked down to form a standard vaccine-type bottle-filling head. the filling head is plugged with a standard rubber-like stopper 36 and sealed with a standard aluminum stopper seal 38. The medicament is sealed into the cartridge 16 at the posterior end by the plunger 32.

Figure 4:
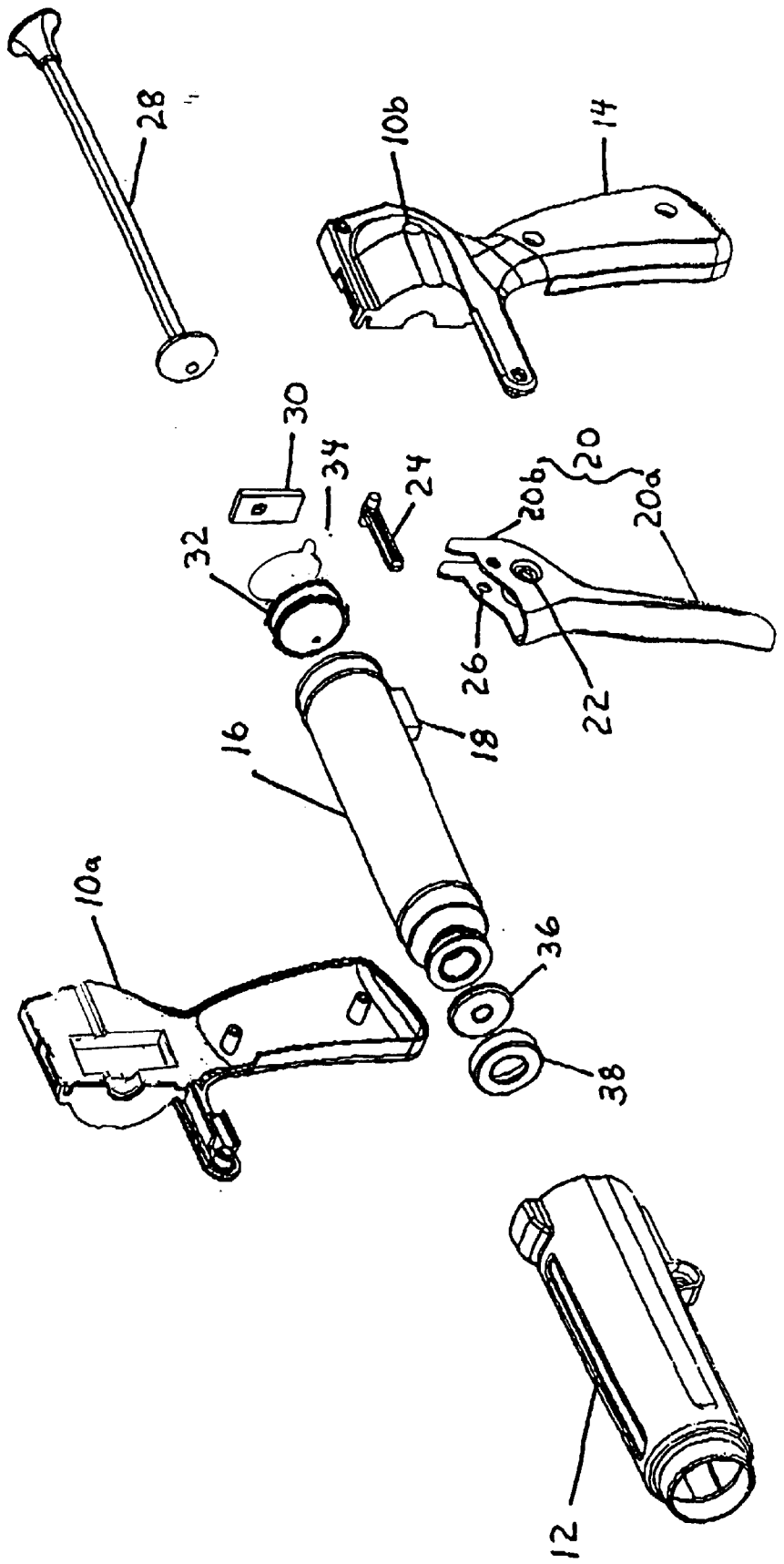
FIG. 4 is a ¾ exploded view of the syringe body, cartridge and self-metering components.

A tear away foil seal 34 is applied to the extreme posterior end of the cartridge 16. the cartridge 16 is molded with a cartridge metering tab 18 on the external surface running parallel to the longitudinal axis of the cartridge 16. The placement of the metering tab 18 on the cartridge 16 dictates the distance the trigger 20 may travel with one full squeeze of the lower trigger 20a, which, in turn, dictates the forward movement of the plunger rod 28. Forward movement of the upper trigger 20b, is transferred to the plunger rod 28 by the drag link 30. The distance the plunger rod 28 may travel dictates the dosage level of medicament dispensed from the cartridge 16. The moveable metering rod 24 is hinged at point 26 on the upper trigger 20b and transfers the movement of the upper trigger 20b, to the metering tab 18. when the moveable metering rod 24 strikes the metering tab 18, the forward movement of the upper trigger 20b and the position of the trigger 20, the drag link 30 and the moveable metering rod 24, all in the resting position. FIG. 2 demonstrates the position of those components in the compressed position i.e., with the lower trigger 20a pulled rearwardly toward the syringe body handle 14. FIG. 4 is an exploded view of the syringe body, cartridge and self-metering components which serves to illustrate the design of those major components associated with the function of the self-metering cartridge.

Operation of Structures of FIGS. 1 to 4

The tear away foil seal 34 is removed from the posterior end of the cartridge 16 and the pre-filled self-metering cartridge 16 is breech loaded into the syringe body barrel 12 and snapped to the closed position to the main syringe body frame 10a and 10b. To administer a dose of medicament the lower trigger 20a is squeezed or compressed to the syringe body handle 14. As the trigger 20 rotates on the trigger pivot 22, the upper trigger 20b moves forward, pushing the drag link 30 forward. the forward angular movement of the drag link 30 creates a bind on the plunger rod 28 and drags the plunger rod 28 forward. The forward movement of the plunger rod 28 pushes the plunger 32 forward in the cartridge 16, forcing the medicament from the cartridge 16 through an adapted needle, pierced into the stopper 36 at the anterior end of the cartridge 16. The moveable metering rod 24 is hinged to the upper trigger 20b at the metering rod hinge point 26. When the trigger 20 is compressed, the moveable metering rod 24 is advanced forward until it makes contact with the cartridge metering tab 18. This contact stops the forward movement of the entire trigger mechanism including the moveable metering rod 24, the trigger 20, the drag link 30, the plunger rod 28 and the plunger 32. thus the positioning of the metering tab 18 along the longitudinal axis of the cartridge 16 determines the travel from the self-metering cartridge 16. The metering rod 24 serves as a detent means for stopping forward movement of the plunger 32 when rod 24 strikes tab 18 on the cartridge 16. Other types of detents could be used, if desired.

The use of this self-metering cartridge of the invention is a tremendous improvement over the current state of the art dosage metering mechanisms available conventional in pistol grip syringes. The advantages listed below become apparent to anyone who has given injections to livestock.

No complicated adjustable metering mechanisms need to be incorporated into the construction of the syringe body.
  There is no chance of the metering adjustment skipping or being bumped into a different setting.
  The possibility of the technician accidentally dialing an improper setting on a metering adjustment is eliminated.
  The dosage level for the medicament is preset and automatic in the cartridge by the manufacturer of the medicament. Therefore, the manufacturer can rest assured that the proper dosage levels of their products are being administered.
  Farm and ranch managers can also rest assured that their employees are administering the proper dosage levels of these expensive medicaments.

Although some example specifications are implied throughout the text of the above descriptions, these should not be construed as limiting the scope of the invention but as merely providing illustrations so that the reader may visualize the embodiment of the invention. Thus, the scope of the invention should be determined by the appended claims and their legal equivalents, rather than by the examples given.

What is claimed is:

1. A system for automatically metering a predetermined dosage of a medicament from a cartridge, the system comprising:
  (a) an elongated cartridge containing said medicament, the cartridge including anterior and posterior ends and a plunger moveable in said cartridge to dispense said medicament through said anterior end;

wherein said cartridge further includes tab means on the exterior thereof:

(b) a pistol grip syringe body capable of receiving said cartridge and including a trigger mounted on said body; said trigger being moveable;

(c) an elongated plunger rod having a forward end axially aligned with said cartridge; and (d) detent means movable by said trigger for stopping forward movement of said plunger when contacting said tab means on said cartridge.

2. An elongated cartridge for containing a medicament, said cartridge including anterior and posterior ends and a plunger positioned therein; wherein said plunger is moveable in said cartridge to dispense said medicament through said anterior end; wherein said cartridge further includes tab means on the exterior thereof and spaced a predetermined distance from said posterior end.

3. A cartridge in accordance with claim 2, wherein said tab means projects outwardly.

4. A pistol grip syringe body dispensing member including a main frame and further comprising:

(a) a tubular barrel portion sized for receiving and supporting an elongated cartridge;

(b) a trigger movably mounted on said frame and being moveable between open and retracted position;

(c) an elongated plunger rod having a forward end;

wherein said plunger rod is axially aligned with said cartridge when positioned in said barrel portion;

(d) detent means being moveable by said trigger and being adapted to stop forward movement of said plunger rod at a predetermined point;

wherein movement of said trigger from said open position to said retracted position causes said plunger rod to advance a plunger in said cartridge a predetermined distance.

5. A method for assuring proper dosage delivery of a medicament to an animal, the method comprising the steps of:

(a) providing a prefilled disposable cartridge containing said medicament; wherein said cartridge includes anterior and posterior ends and a plunger positioned in said posterior end; wherein said plunger is movable in said cartridge to dispense said medicament through said anterior end; wherein said cartridge further includes tab means on the exterior thereof;

(b) providing a dispensing gun capable of receiving and supporting said cartridge; wherein said gun includes a plunger rod which is axially movable and trigger means adapted to advance said plunger rod;

wherein said trigger means is movable between open and retracted positions; wherein said gun further includes detent means movable by said trigger for stopping forward movement of said plunger when said detent means contacts said tab means on said cartridge;

(c) coupling said cartridge to said gun; and (d) moving said trigger from said open position to said retracted position to dispense a predetermined dosage of said medicament.

* * * * *